United States Patent
Parker

(10) Patent No.: US 8,057,528 B2
(45) Date of Patent: Nov. 15, 2011

(54) BALLOON-STENT COMBINATION

(75) Inventor: Fred T. Parker, Unionville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1121 days.

(21) Appl. No.: 11/764,591

(22) Filed: Jun. 18, 2007

(65) Prior Publication Data

US 2007/0293931 A1    Dec. 20, 2007

Related U.S. Application Data

(60) Provisional application No. 60/815,294, filed on Jun. 20, 2006.

(51) Int. Cl.
*A61F 2/06* (2006.01)

(52) U.S. Cl. .................................................. 623/1.12

(58) Field of Classification Search ................ 623/1.11, 623/1.12, 1.13, 1.23, 1.25; 606/191, 192, 606/194, 195

See application file for complete search history.

(56) References Cited

U.S. PATENT DOCUMENTS

| | | | |
|---|---|---|---|
| 4,130,904 A | 12/1978 | Whalen | |
| 4,300,244 A | 11/1981 | Bokros | |
| 5,123,917 A | 6/1992 | Lee | |
| 5,282,824 A | 2/1994 | Gianturco | |
| 5,415,664 A | 5/1995 | Pinchuk | |
| 5,693,085 A * | 12/1997 | Buirge et al. | 623/1.13 |
| 5,993,484 A * | 11/1999 | Shmulewitz | 623/1.11 |
| 6,063,112 A | 5/2000 | Sgro | |
| 6,206,931 B1 | 3/2001 | Cook et al. | |
| 6,790,224 B2 * | 9/2004 | Gerberding | 623/1.12 |
| 7,201,770 B2 * | 4/2007 | Johnson et al. | 623/1.12 |
| 7,351,255 B2 * | 4/2008 | Andreas | 623/1.12 |
| 2004/0267195 A1 | 12/2004 | Currlin | |
| 2005/0154414 A1 * | 7/2005 | Perreault et al. | 606/192 |
| 2005/0246009 A1 * | 11/2005 | Toner et al. | 623/1.11 |
| 2006/0190030 A1 * | 8/2006 | To et al. | 606/205 |
| 2006/0212112 A1 * | 9/2006 | Evans et al. | 623/1.25 |

* cited by examiner

*Primary Examiner* — Gary Jackson
*Assistant Examiner* — Katherine Dowe
(74) *Attorney, Agent, or Firm* — Brinks Hofer Gilson & Lione

(57) ABSTRACT

The present invention provides apparatus and methods for treating a vascular condition formed within a vessel by providing a balloon having proximal and distal regions and a stent configured to be disposed within the balloon. When the balloon is partially or fully inflated, the stent may be advanced within the confines of the balloon and then expanded to engage an inner surface of the balloon. The stent urges the balloon against the vessel wall, and the proximal and distal regions of the balloon then are cut to leave the balloon and stent within the vessel. The balloon may comprise a collagenous extracellular matrix material to facilitate fusion of the balloon with the vessel wall.

14 Claims, 12 Drawing Sheets

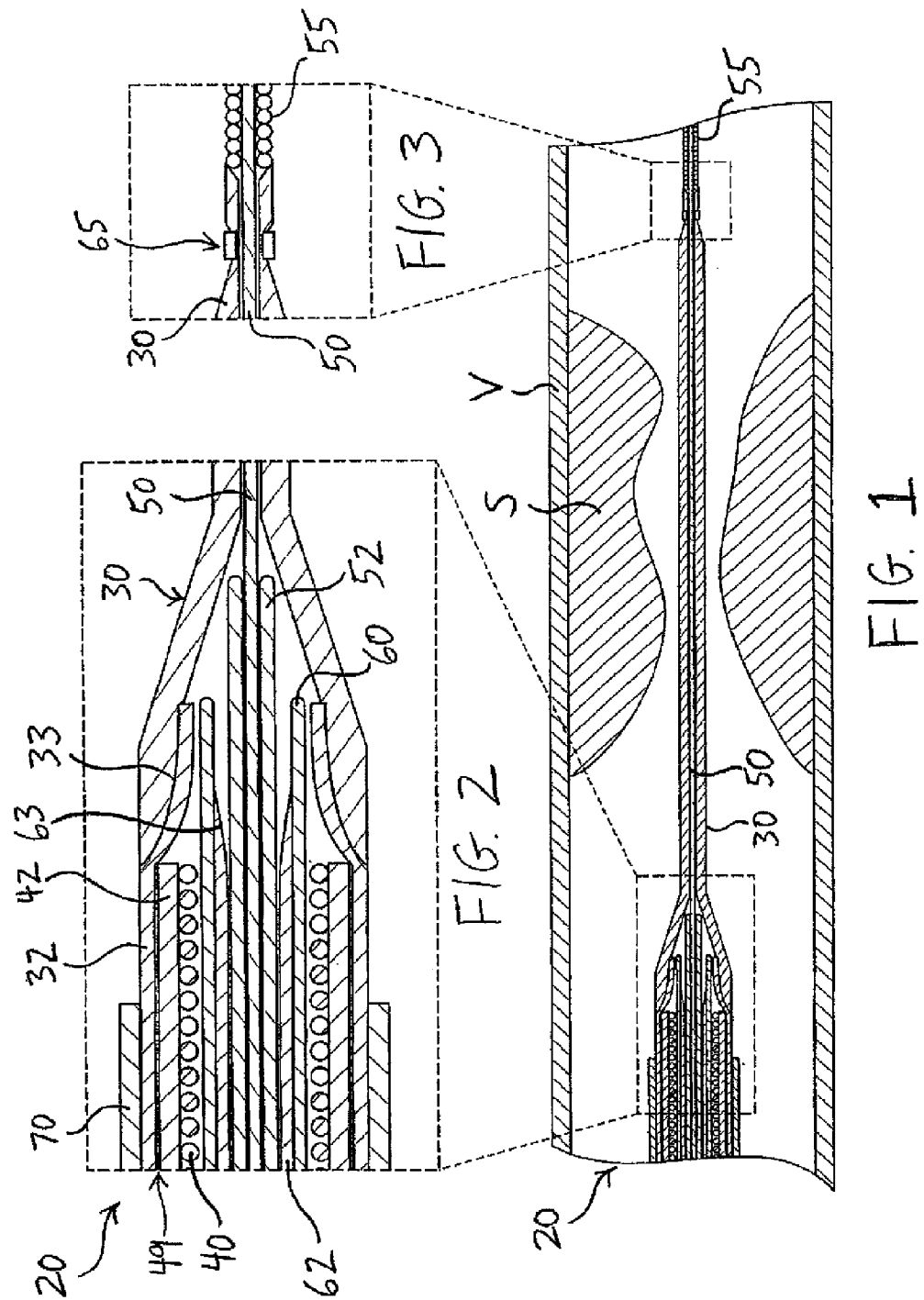

BALLOON-STENT COMBINATION

PRIORITY CLAIM

This invention claims the benefit of priority of U.S. Provisional Application Ser. No. 60/815,294, entitled "Balloon-Stent Combination," filed Jun. 20, 2006, the disclosure of which is hereby incorporated by reference in its entirety.

BACKGROUND

The present invention relates generally to apparatus and methods for treating vascular conditions, and more specifically, to a balloon-stent combination that treats the vascular condition and leaves at least a portion of the balloon inside the vessel after treatment.

Atherosclerosis and other occlusive diseases are prevalent among a significant portion of the population. In such diseases, atherosclerotic plaque forms within the walls of the vessel and blocks or restricts blood flow through the vessel. Atherosclerosis commonly affects the coronary arteries, the aorta, the iliofemoral arteries and the carotid arteries. Several serious conditions may result from the restricted blood flow, such as ischemic events.

Various procedures are known for treating stenoses in the arterial vasculature, such as the use of atherectomy devices, balloon angioplasty and stenting. During an atherectomy procedure, vascular plaque may be removed by inserting a catheter having a rotating cutting blade into the vessel and using the blade to shave away the plaque. During a balloon angioplasty procedure, a catheter having a deflated balloon attached thereto is positioned across a constricting lesion, and the balloon is then inflated to widen the lumen to partially or fully restore patency to the vessel.

Stenting involves the insertion of a usually tubular member into a vessel, and may be used alone or in conjunction with an angioplasty procedure. Stents may be self-expanding or balloon expandable. Self-expanding stents typically are delivered into a vessel within a delivery sheath, which constrains the stent prior to deployment. When the delivery sheath is retracted, the stent is allowed to radially expand to its predetermined shape. If the stent is balloon expandable, the stent typically is loaded onto a balloon of a catheter, inserted into a vessel, and the balloon is inflated to radially expand the stent.

Many recent self-expanding and balloon expandable stents have been coated using various agents, such as drugs or bioactive materials, to achieve a biological effect in addition to applying a radially outward force. Such drug coated stents may deliver the agents in close proximity to a stenotic lesion to reduce the likelihood of restenosis.

One problem frequently encountered with atherectomy, angioplasty and stenting procedures is that pieces of plaque are often dislodged from the stenosis. Such pieces of plaque, referred to as emboli, may flow away from the stenosis into other areas of the vasculature and may be difficult to retrieve. Serious complications, such as heart attack and stroke, may occur where the emboli travel into the coronary or carotid arteries.

Several techniques exist for retrieving emboli during a medical procedure, such as deploying a filter within the vasculature distal to the stenosis. However, an important consideration is reducing the amount of emboli that becomes dislodged into the vasculature, and many filters may compound the problem by dislodging plaque as the filter traverses the stenosis. There is a need for apparatus and methods that effectively treat a vascular condition by restoring patency to the vessel while reducing the likelihood that emboli becomes dislodged into the bloodstream.

SUMMARY

The present invention provides apparatus and methods for treating a vascular condition, such as a stenosis formed within a vessel, by providing a balloon having proximal and distal regions and a stent configured to be disposed within the balloon. Means for detaching at least a portion of the balloon are provided. After the stent is expanded within the balloon, the means for detaching leaves the portion of the balloon inside the vessel.

In one embodiment, the apparatus comprises a balloon shaft having proximal and distal ends, and a core wire having proximal and distal ends, wherein the core wire is disposed substantially within the balloon shaft. The distal end of the core wire extends past the distal end of the balloon shaft. The proximal region of the balloon is attached to the balloon shaft and the distal region of the balloon is attached to the core wire.

The stent is configured to be advanced within the confines of the balloon. In one embodiment, the stent comprises a self-expanding stent that is introduced in a constrained state using a stent introducer. When the stent is positioned within a portion of the balloon, the stent introducer may be retracted proximally to cause the stent to radially expand and engage an inner surface of the balloon. The stent therefore urges the balloon radially outward against an inner surface of the vessel in the expanded state, for example, to dilate a stenosis. The balloon may also be used to dilate the stenosis. The means for detaching is actuated to leave a portion of the balloon inside the vessel between the stent and the intima of the vessel.

In a preferred embodiment, at least a portion of the balloon comprises a collagenous extracellular matrix material ("ECM") to facilitate fusion of the portion of the balloon with the intima of the vessel. Preferably, the ECM material causes a proximal portion of the balloon to fuse with the vessel wall at a location proximal to a stenosis, and causes a distal portion of the balloon to fuse with the vessel wall distal to the stenosis, thereby effectively sealing off the stenosis from blood flow and reducing the likelihood of subsequent embolization.

In one embodiment, the means for detaching comprises a distal cutting cannula having proximal and distal ends and a piercing element disposed at the distal end. The distal cutting cannula is disposed annularly between the balloon shaft and the core wire. When the balloon is inflated, the distal cutting cannula may be advanced distally to cause the piercing element to pierce through a distal portion of the balloon to sever the distal portion of the balloon. A proximal cutting cannula also may be employed to sever the proximal portion of the balloon.

In an alternative embodiment, the means for detaching comprises one or more perforations formed in the balloon. In this embodiment, inflation of the balloon beyond a predetermined pressure may cause the perforations to tear apart to detach the portion of the balloon. Alternatively, when the stent is expanded inside the balloon, the internal pressure of the stent against the balloon may cause the perforations to tear apart.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 1 is a side-sectional view of an apparatus that may be used to treat a vascular condition formed within a vessel.

FIG. 2 is an enlarged side-sectional view of the apparatus of FIG. 1.

FIG. 3 is an enlarged side-sectional view of the apparatus of FIG. 1.

DETAILED DESCRIPTION OF THE PREFERRED EMBODIMENTS

Figure 4:
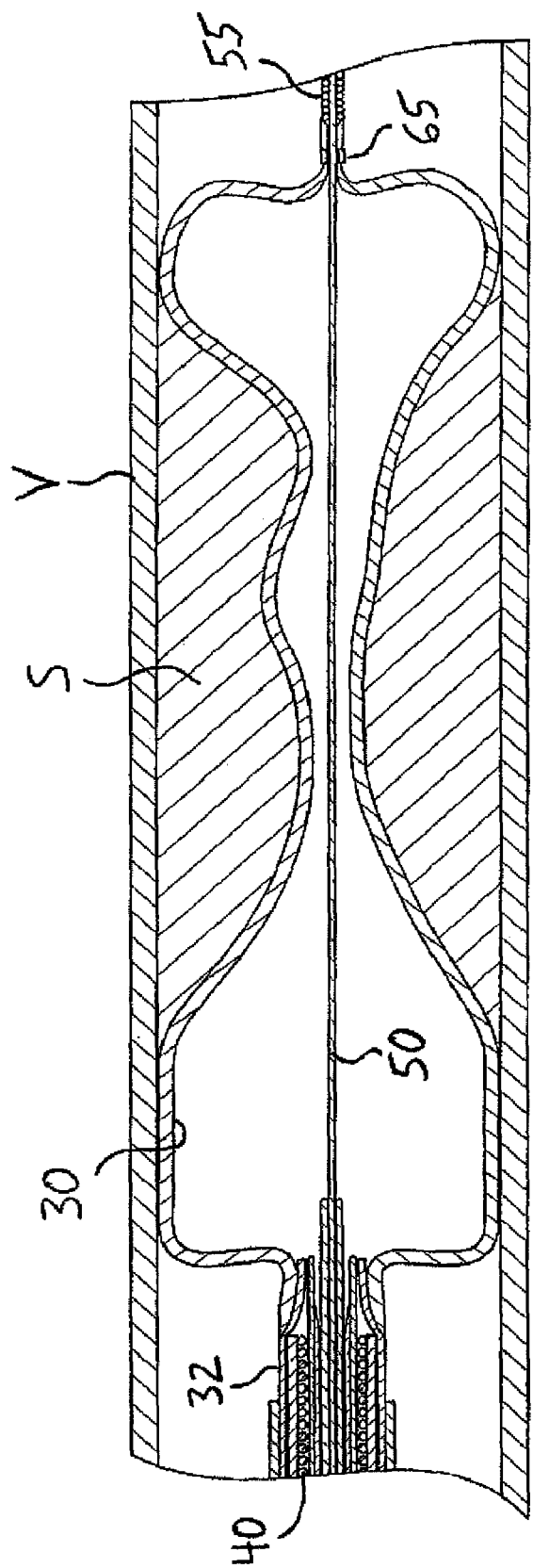
FIGS. 4-13 are side-sectional views illustrating method steps that may be used to treat a vascular condition using the apparatus of FIGS. 1-3.

In the present application, the term "proximal" refers to direction that is generally towards a physician during a medical procedure, while the term "distal" refers to a direction that is generally towards a target site within a patent's anatomy during a medical procedure.

Referring now to FIGS. 1-3, apparatus suitable for treating a vascular condition, such as stenosis S within vessel V, are described. Apparatus 20 comprises balloon 30, stent 40 and core wire 50. Balloon 30 preferably is disposed on a distal region of balloon shaft 32, which has proximal and distal ends. Balloon shaft 32 may comprise distal taper 33, which tapers radially inward, so that the attachment of balloon 30 to balloon shaft 32 does not increase the radial profile of the delivery system, as shown in FIG. 2.

Balloon shaft 32 may be manufactured from any suitable material used in the manufacture of catheters, such as polyurethane, polyethylene, tetrafluoroethylene, polytetrafluoroethylene, perfluoalkoxl, fluorinated ethylene propylene, or the like. Similarly, balloon 30 may be manufactured from any suitable balloon material used during an interventional procedure. However, in a preferred embodiment, balloon 30 comprises a collagenous extracellular matrix material (ECM), such as small intestinal submucosa (SIS), which may facilitate attachment of balloon 30 to the intima of vessel V, as explained in detail below.

Apparatus 20 her comprises at least one stent 40 that has a delivery state, as shown in FIG. 2, and further has an expanded state in which it is configured to expand radially outward to engage an inner lumen of vessel V. Various types of stents 40 may be used in conjunction with the present invention. For example, stent 40 may be made from numerous metals and alloys, including stainless steel, nitinol, cobalt-chrome alloys, amorphous metals, tantalum, platinum, gold and titanium. The stent may also be made from non-metallic materials, such as thermoplastics and other polymers. The structure of stent 40 may also be formed in a variety of ways to provide a suitable intraluminal support structure. For example, stent 40 may be made from a woven wire structure, a laser-cut cannula, individual interconnected rings, or any other type of stent structure that is known in the art.

As depicted in FIGS. 7-13 below, stent 40 is shown having a generally zig-zag shape for illustrative purposes. As will be apparent to one skilled in the art, stent 40 may alternatively comprise any number of shapes that may vary depending on the needs of the procedure.

Stent 40 may also be designed to be either balloon-expandable or self-expandable. In a preferred embodiment, stent 40 is self-expandable and is formed from a shape-memory alloy, such as nickel-titanium (nitinol). In FIG. 2, stent 40 comprises a self-expanding stent that is constrained by stent introducer 42. Stent introducer 42 comprises a tubular member disposed within balloon shaft 32 and restricts radial expansion of stent 40 until retracted proximally, as described below with respect to FIG. 7.

Figure 5:
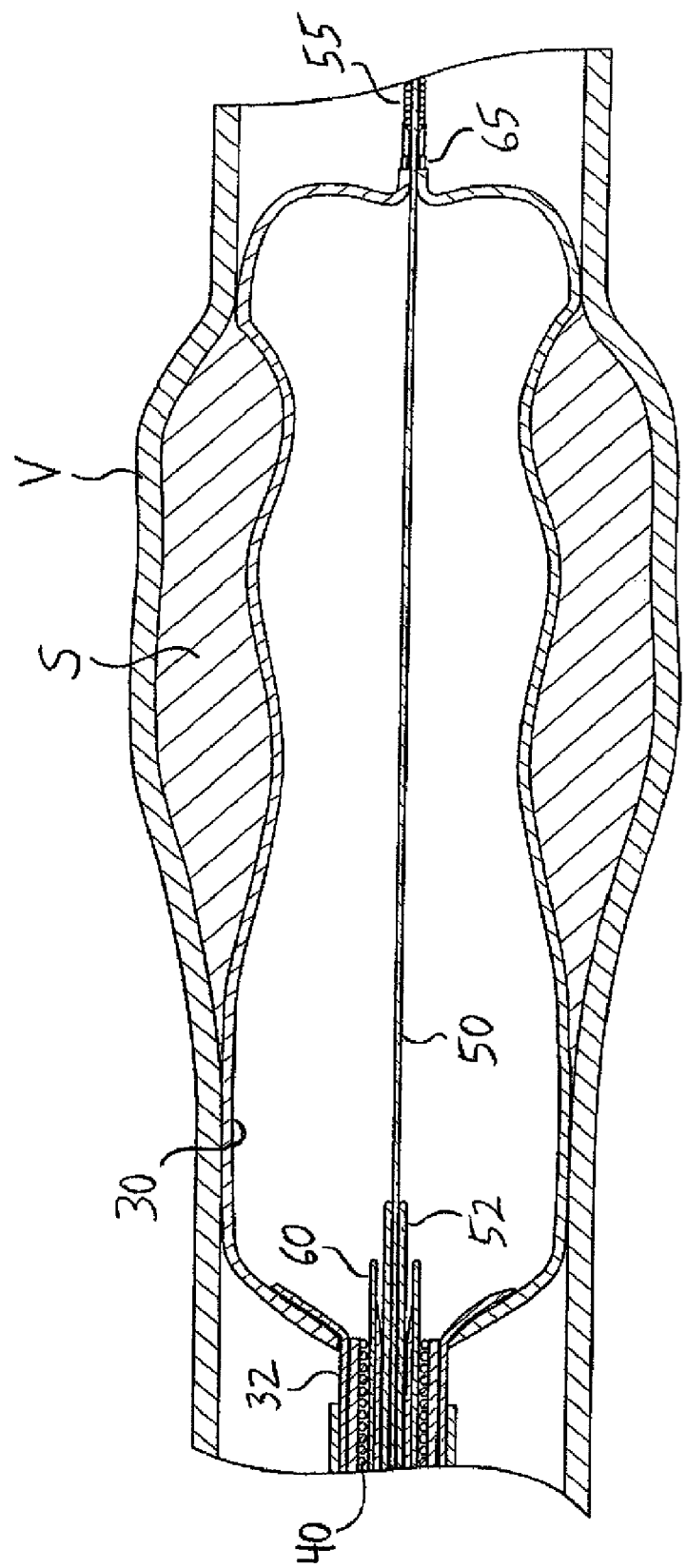

In a preferred embodiment, annular inflation lumen 49 is formed between balloon shaft 32 and stent introducer 42, as shown in FIG. 2. An inflation fluid may be injected through a proximal port (not shown), which directs the inflation fluid through annular inflation lumen 49 in a distal direction. When the inflation fluid passes distal to stent introducer 42, the inflation fluid may flow around the distal end of shielding cannula 60 and centering cannula 52 and into an annular space between core wire 50 and balloon 30, thereby causing balloon 30 to inflate as shown in FIGS. 4-5 below. As will be apparent to one skilled in the art, an alternative inflation channel may be employed, such as an inflation tube (not shown) disposed between the proximal end of apparatus 20 and balloon 30.

Referring still to FIGS. 1-3, apparatus 20 further comprises core wire 50. In a preferred embodiment, core wire 50 comprises a solid wire that spans from the proximal end of apparatus 20 and transitions into wire guide tip 55 at the distal end of apparatus 20, as depicted in FIGS. 1 and 3. Alternatively, a separate wire guide component may be disposed through a dedicated wire guide lumen (not shown).

In operation, core wire 50 serves various functions. First, core wire 50 provides longitudinal pushability and flexibility when apparatus 20 is guided through tortuous anatomy. Further, core wire 50 guides and centers various tubular components of apparatus 20, as shown in FIG. 2 and described below.

The distal end of balloon 30 preferably is secured around core wire 50 using constraint band 65, as shown in FIG. 3. Constraint band 65 may comprise a radiopaque marker to indicate when the distal end of balloon 30 is positioned distal to stenosis S, as depicted in FIG. 1.

Figure 8:
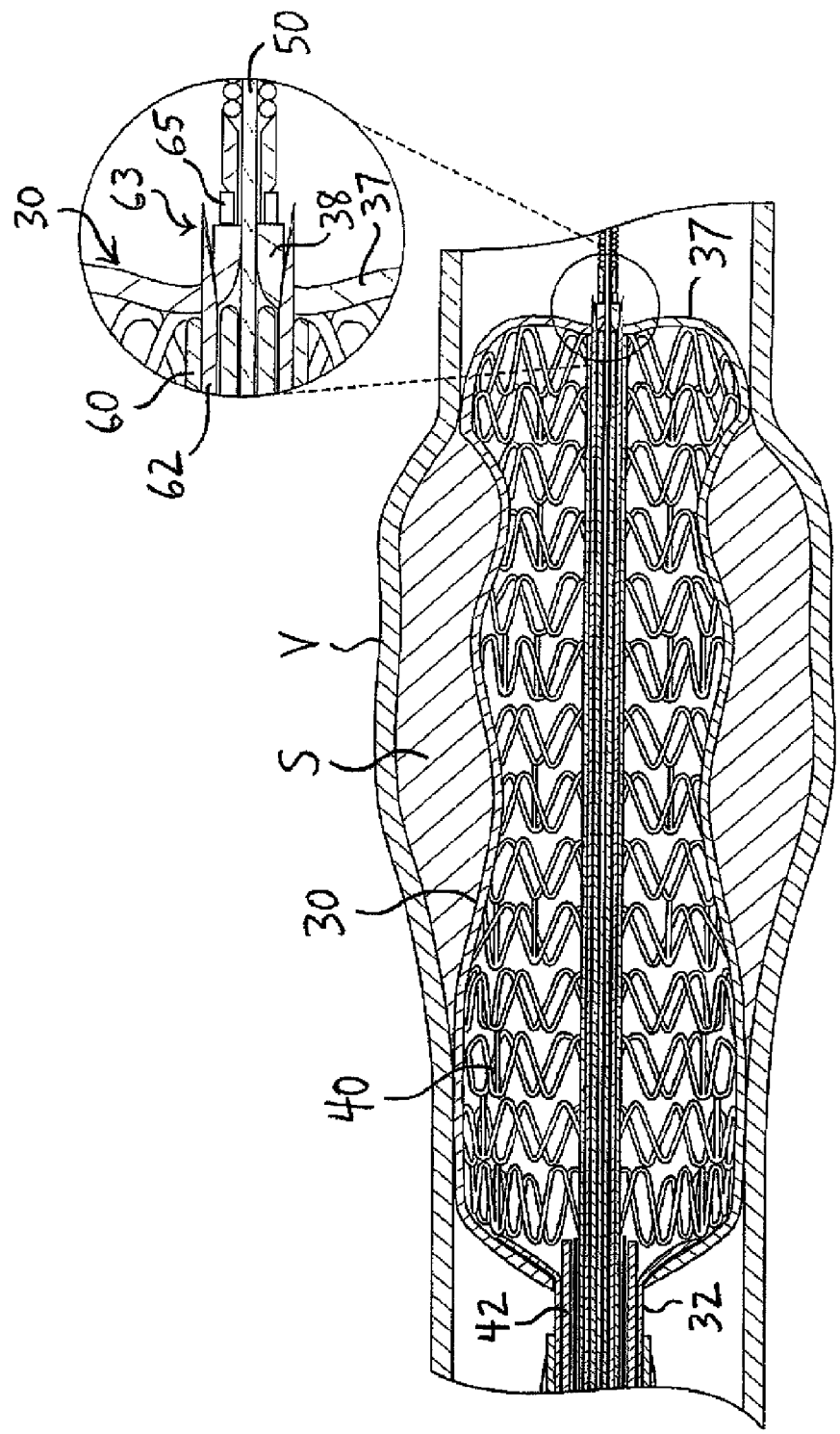

Referring still to FIG. 2, apparatus 20 further comprises shielding cannula 60, distal cutting cannula 62 and, optionally, centering cannula 52, which may be employed to provide added pushability to the distal end of apparatus 20. Distal cutting cannula 62 preferably comprises a tubular member having proximal and distal ends and piercing element 63 disposed on the distal end, as best seen in FIG. 8. Piercing element 63 may be formed integral with the distal end of distal cutting cannula 62 or may comprise a sharpened element attached to the distal end of the cannula.

Distal cutting cannula 62 is disposed annularly between shielding cannula 60 and centering cannula 52 (if centering cannula 52 is omitted, distal cutting cannula 62 may be disposed adjacent core wire 50), as shown in FIG. 2. During delivery of apparatus 20, shielding cannula 60 extends distal to piercing element 63 to ensure that piercing element 63 does not inadvertently pierce a hole in balloon 30.

It should be noted that cannulas 52, 60 and/or 62 need not be solid along their longitudinal length. For example, the cannulas may be laser cut in a pattern designed to provide added axial flexibility, or may employ multiple materials along their lengths, to facilitate advancement through tortuous anatomy.

Referring now to FIGS. 4-13, a method for using apparatus 20 to treat a vascular condition, such as stenosis S in vessel V, is described. In FIG. 1, the distal portion of apparatus 20 is shown guided into vessel V in a delivery state. As mentioned above, wire guide 55 helps guide apparatus 20 through a patient's vasculature and into vessel V. Wire guide 55 traverses stenosis S, preferably using fluoroscopic guidance, and is disposed distal to the stenosis, as shown in FIG. 1. A portion of balloon 30, which is disposed around core wire 50, also crosses stenosis S.

Apparatus 20 is positioned such that the distal end of balloon 30 is disposed distal to stenosis S. As noted above, constraint band 65 may comprise a radiopaque marker to facilitate positioning of balloon 30. At this time, the remaining components of apparatus 20, including stent 40 and the various cannulas, are disposed proximal of stenosis S, as shown in FIG. 1. If desired, centering cannula 52 and/or shielding cannula 60 may be advanced distally to traverse stenosis S and provide added pushability while partially dilating stenosis S. As soon as the balloon starts to cross the stenosis, blood flow is restricted and may be shut off by the balloon. Since there is little or no blood flow, any stenosis that breaks free is less likely to migrate. This technique may also be beneficial for safer crossing of a stenosis by a filter device.

After positioning apparatus 20 within vessel V, balloon 30 is inflated through inflation lumen 49, as depicted in FIGS. 4-5. In FIG. 4, balloon 30 is partially inflated and begins to conform to the shape of stenosis S, while in FIG. 5, balloon 30 is shown dilating the stenosis and urging vessel V in a radially outward direction. Optionally, one or more small perforations (not shown) may be formed in the distal end of balloon 30, at a location just proximal to constraint band 65, to permit oxygenated fluid to flow upstream to arterial vasculature during treatment of stenosis S. The oxygenated fluid may also be the balloon dilation fluid.

It should be noted that the dilation force provided by balloon 30 against stenosis S need not be as high as during a conventional angioplasty procedure. This is because, in a subsequent step, stent 40 is deployed to partially or fully dilate the stenosis. The dilation force provided by balloon 30 preferably expands stenosis S enough to easily permit advancement of multiple components over core wire 50 and through the stenosis without disrupting it or dislodging plaque, as explained below.

Figure 6:
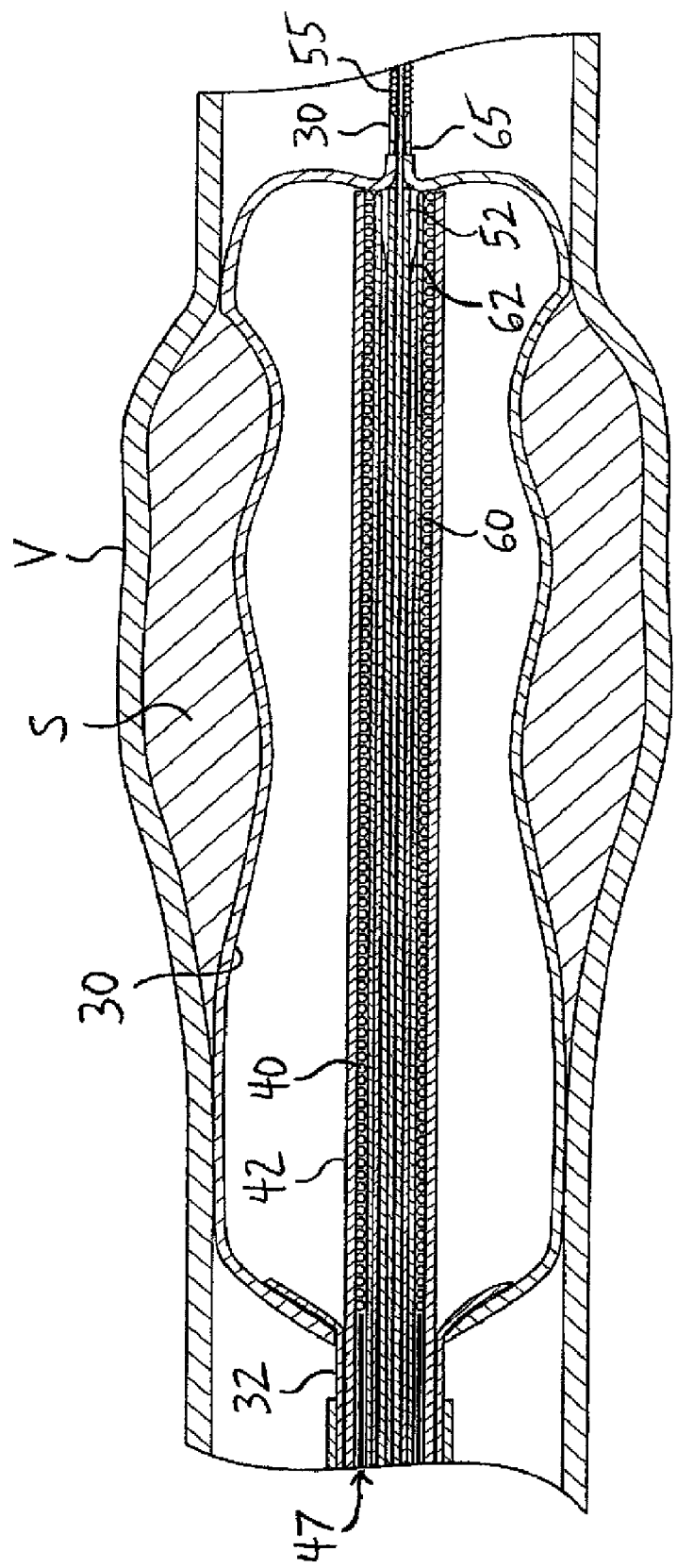

Referring now to FIG. 6, in a next step, while balloon 30 is dilating stenosis S, multiple components are advanced distally through stenosis S, i.e., within the confines of balloon 30 and over core wire 50. Specifically, centering cannula 52, shielding cannula 60 and distal cutting cannula 62 are advanced via core wire 50 towards the distal end of balloon 30, as shown in FIG. 6. Also, stent introducer 42 having stent 40 constrained therein is advanced towards the distal end of balloon 30.

Figure 7:
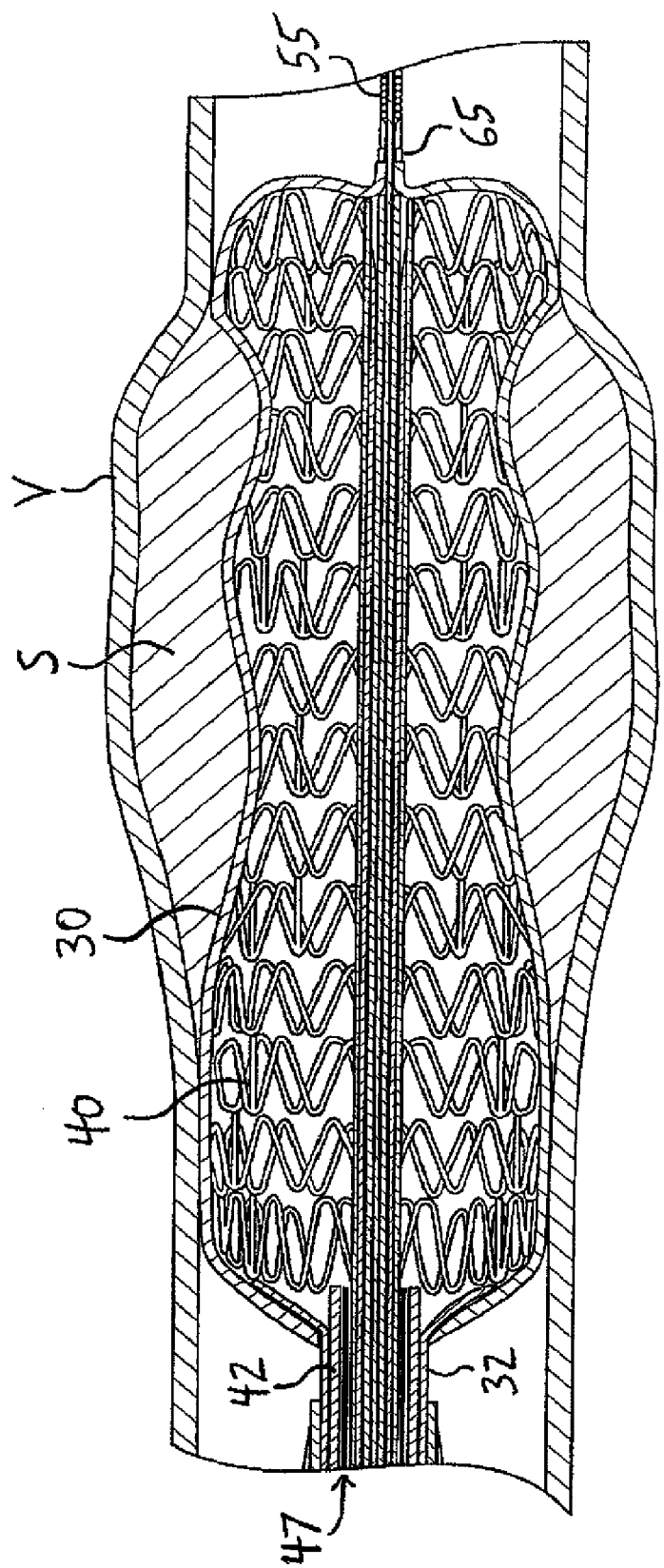

In a next step, shown in FIG. 7, stent 40 is deployed by proximally retracting stent introducer 42 with respect to stent 40. Preferably, pusher tube 47 is disposed within stent introducer 42 at a location proximal to stent 40. In operation, pusher tube 47 is held steady while stent introducer 42 is retracted proximally to ensure that the stent does not shift proximally during deployment. In this embodiment, stent 40 self-expands when no longer radially constrained. In the deployed state, stent 40 engages an inner surface of balloon 30 and serves to dilate stenosis S.

Figure 9:
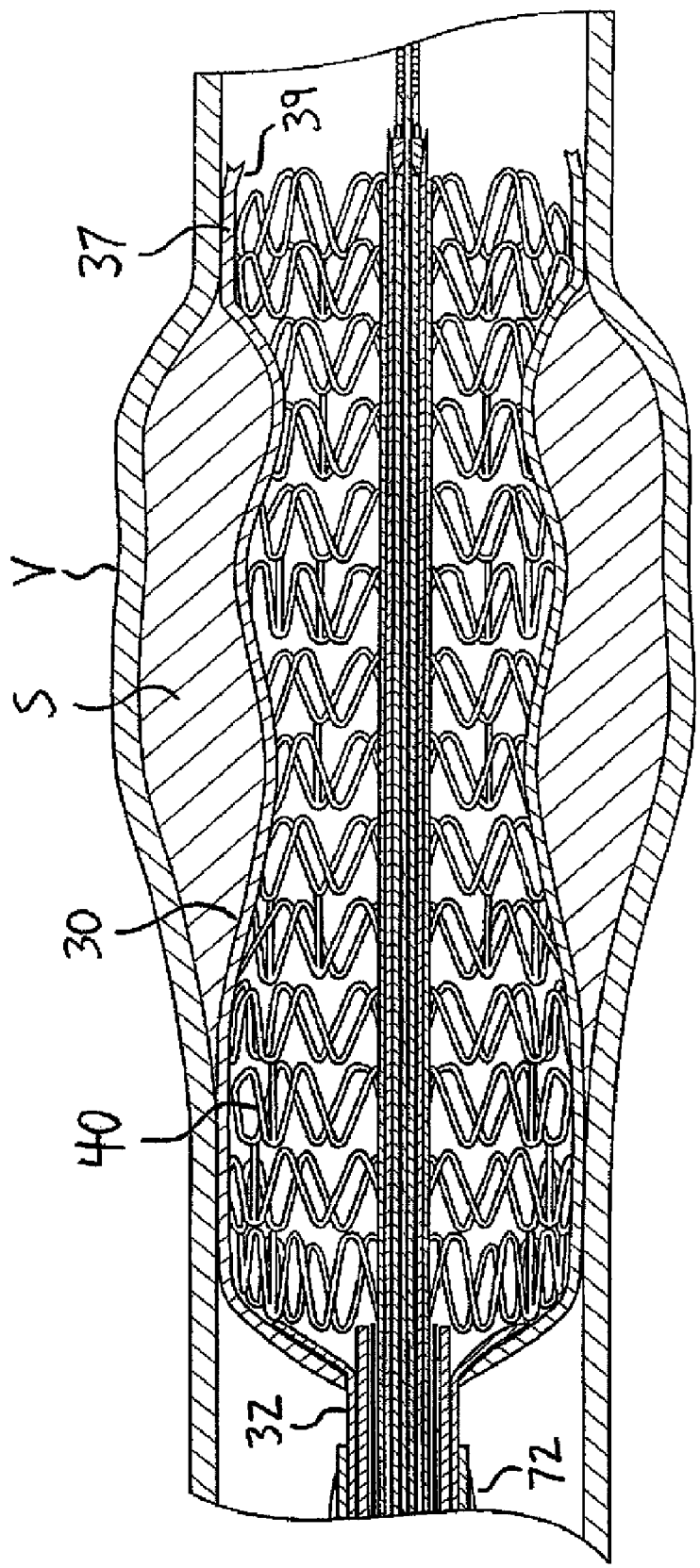

Referring now to FIGS. 8-9, after stent 40 is deployed, distal cutting cannula 62 is advanced distally with respect to shielding cannula 60 to cause piercing element 63 to pierce the distal end of balloon 30. Preferably, piercing element 63 is circumferentially-shaped to cut through balloon 30. At this time, balloon 30 is severed into portions 37 and 38, which are located proximal and distal to the piercing location, respectively. Balloon portion 38 remains attached to core wire 50 via constraint band 65, as shown in FIG. 8. Balloon portion 37, by contrast, is urged in a radially outward direction by deployed stent 40, as shown in FIG. 9.

Preferably, an outer surface of balloon portion 37 comes into contact with the intima of vessel V to facilitate attachment of balloon 30 within the vessel at a location distal to stenosis S. As will be explained in greater detail below, balloon 30 preferably comprises a collagenous extracellular matrix material (ECM), such as small intestinal submucosa (SIS), which may facilitate attachment of balloon 30 to the intima of vessel V.

After the distal end of balloon 30 has been severed and stent 40 urges balloon portion 37 against the intima of vessel V, a small portion 39 of balloon 30 may bow radially inward because it extends distal to stent 40, as depicted in FIG. 9. In this case, a physician may subsequently cut portion 39, if possible, or use a means to apply a radially outward pressure against portion 39 to promote engagement with vessel V. Alternatively, a physician may choose to do nothing and leave portion 39 to fuse with vessel V over time.

At this time, cannulas 52, 60 and 62 may be retracted proximally so that they are housed entirely within the confines of balloon shaft 32. Alternatively, the distal end of shielding cannula 60 may be advanced with respect to distal cutting cannula 62 to fully enclose piercing element 63 and reduce the likelihood of accidentally puncturing the vessel wall.

Figure 10:
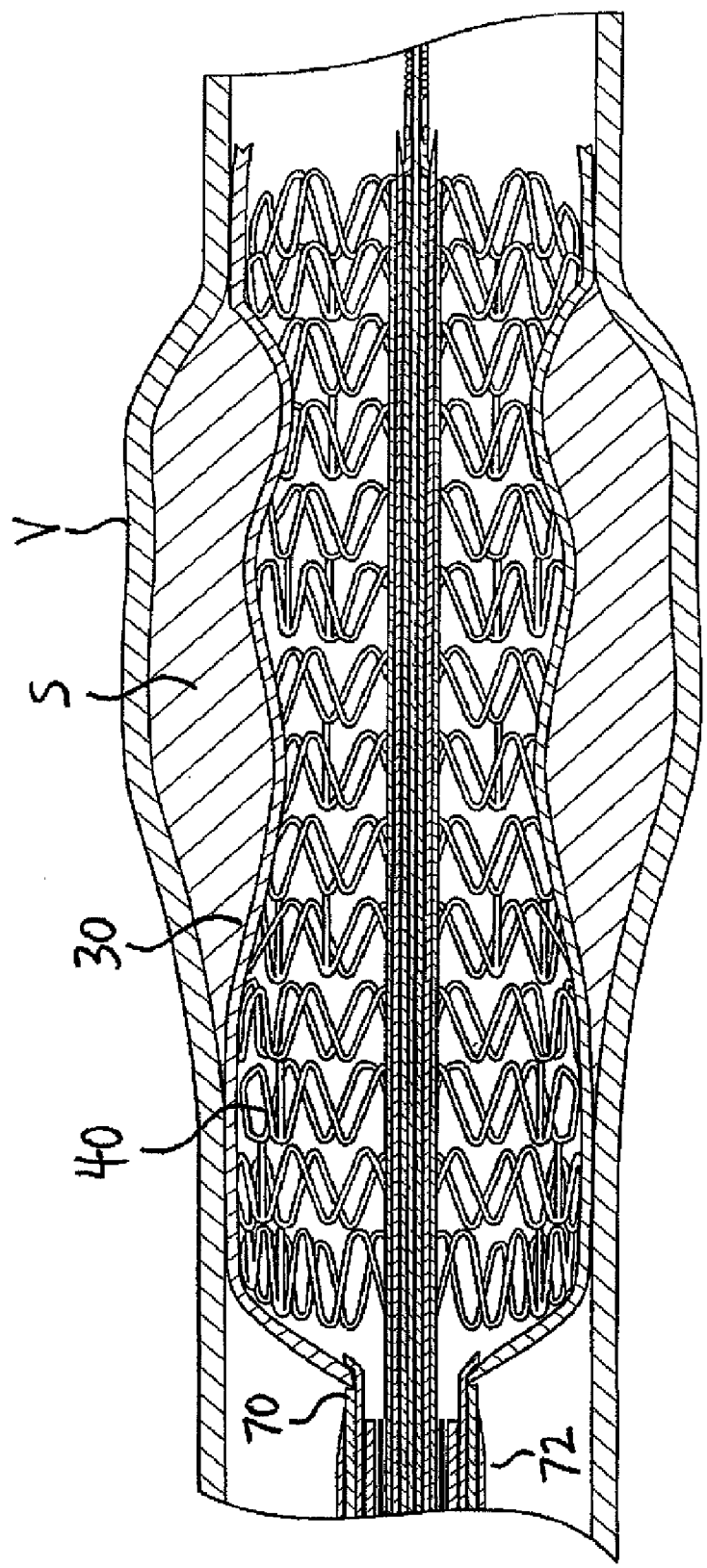
Figure 11:
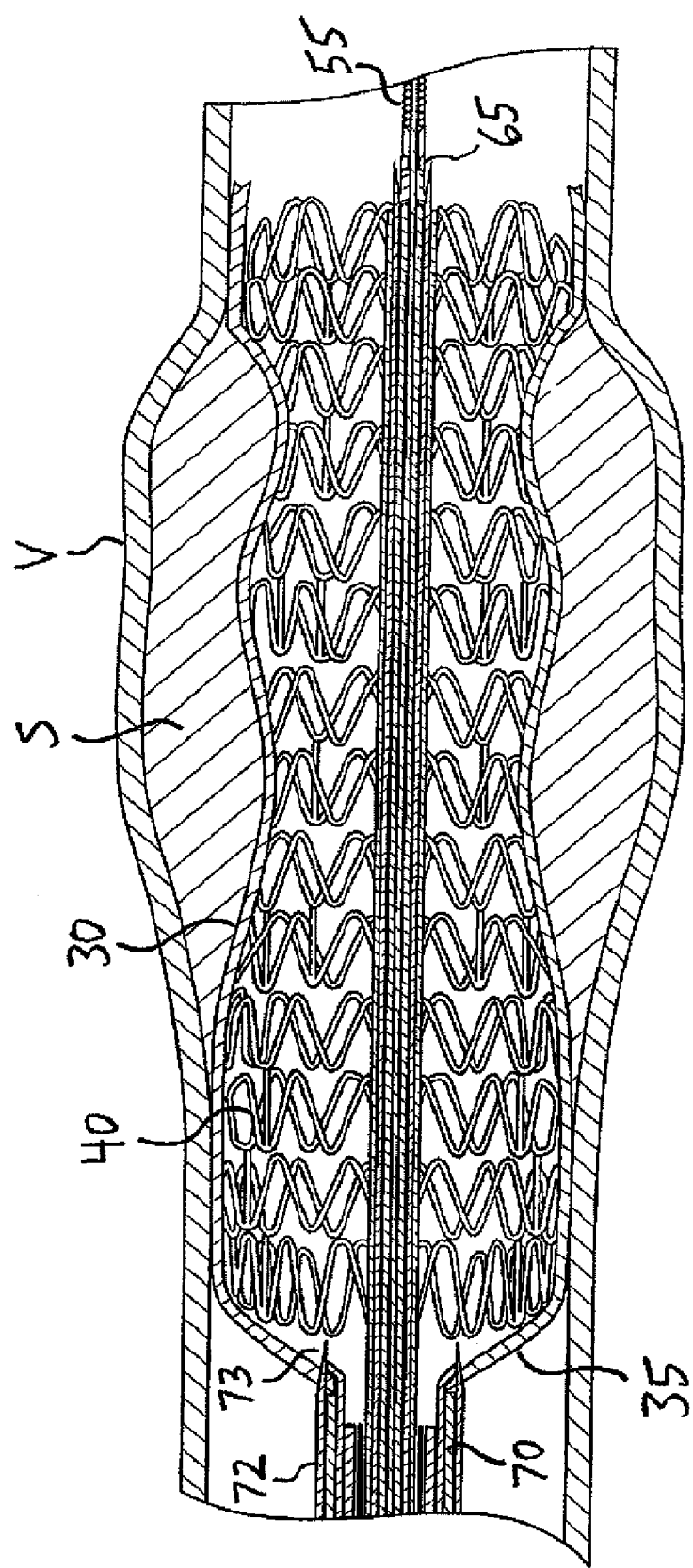
Figure 12:
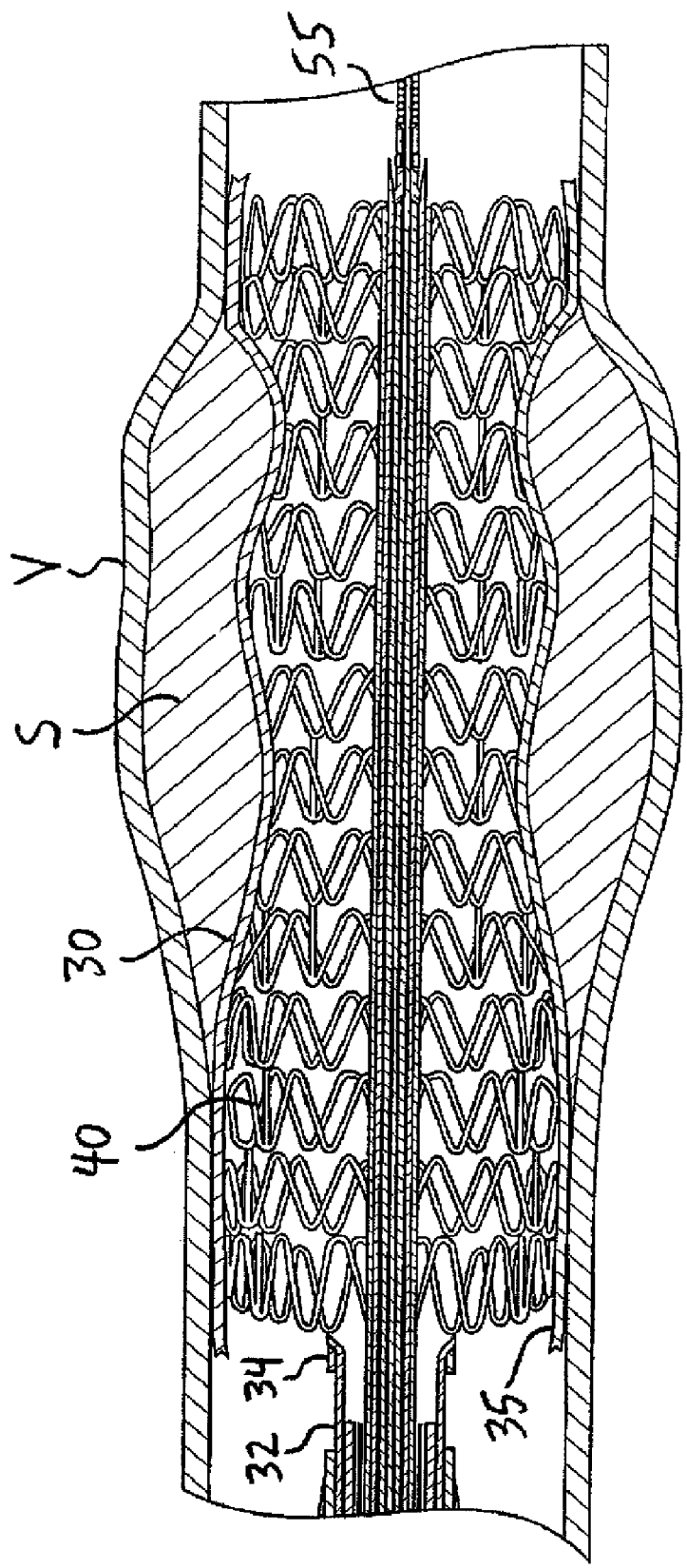

Referring now to FIGS. 10-12, in a next step, proximal guide cannula 70 is advanced distally until it engages the proximal end of balloon 30, as shown in FIG. 10. Then, proximal cutting cannula 72, having piercing element 73 disposed at its distal end, is advanced distally. Piercing element 73 is configured to cut through a proximal region of balloon 30, as shown in FIG. 11, in the same manner that piercing element 63 cut through the distal region of balloon 30, as explained in FIG. 8 above.

In FIG. 12, the proximal region of balloon 30 is severed into portions 34 and 35, which are located proximal and distal to the piercing location, respectively. Balloon portion 34, which is proximal to the location of the cut, remains attached to balloon shaft 32 at tapered attachment point 33 (see FIG. 2). Balloon portion 35, which is distal to the location of the pierce, is urged in a radially outward direction by deployed stent 40, as shown in FIG. 12. Preferably, an outer surface of balloon portion 35 comes into contact with the intima of vessel V to facilitate attachment of balloon 30 within the vessel at a location proximal to stenosis S. A physician may subsequently use a means to apply a radially outward pressure against portion 35 to promote engagement with vessel V, or may leave portion 35 to fuse with vessel V over time.

Figure 13:
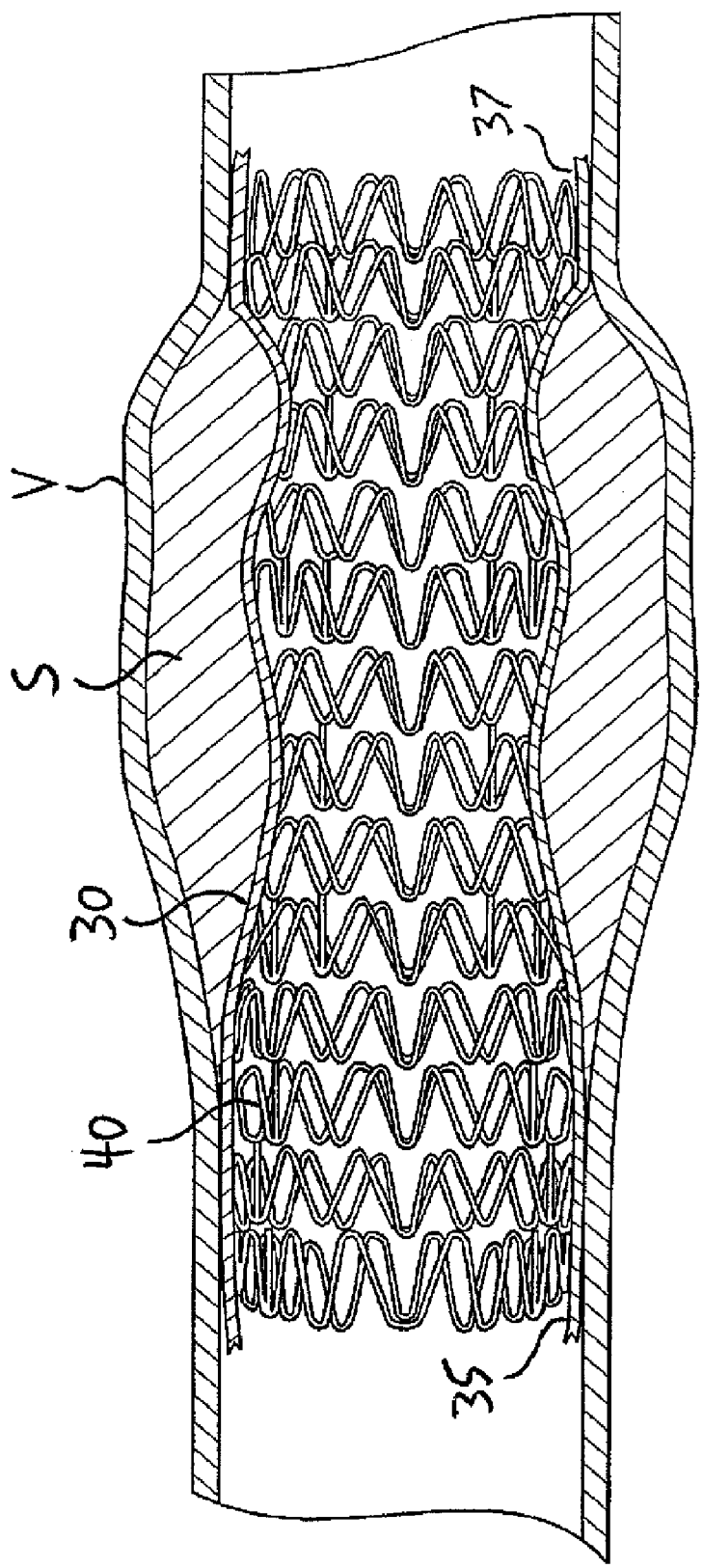

In a final step, the delivery components, including balloon shaft 32, stent introducer 42, core wire 50, and all of the cannulas are removed from the patient's vessel (if not previously removed in a prior step). As shown in FIG. 13, balloon 30 and stent 40 are left in place within vessel V, with balloon 30 being disposed substantially between stent 40 and stenosis S. Proximal balloon portion 35 and distal balloon portion 37 engage the intima of vessel V at locations proximal and distal to stenosis S, respectively, to seal off the stenosis and ensure that embolic matter will not be dislodged into the bloodstream.

As mentioned above, balloon 30 preferably is manufactured using a material, or comprises a coating, that facilitates attachment of an outer surface of balloon 30 to the intima of vessel V. In a preferred embodiment, reconstituted or naturally-derived collagenous materials can be used in the present invention. Such materials that are at least bioresorbable will provide an advantage in the present invention, with materials that are bioremodelable and promote cellular invasion and ingrowth providing particular advantage.

Suitable bioremodelable materials can be provided by collagenous ECMs possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including SIS, stomach submucosa, urinary bladder submucosa, and uterine submucosa.

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multiaxial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material. See, C. Heeschen et al., Nature Medicine 7(2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics or thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the material in the patient.

Submucosa or other ECM tissue that may be used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 μg/mg, more preferably less than about 2 μg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

If balloon 30 of the present invention employs SIS material, then in order to pressurize the SIS material, it may be treated with a biodegradable solution such as polyvinylpyrrolidone (PVP). As will be apparent, the entirety of balloon 30 may be manufactured from an ECM material such as SIS, or alternatively, selected portions may be manufactured from the ECM material or may be selectively coated with the material to promote localized fusion with vessel V.

Figure 14:
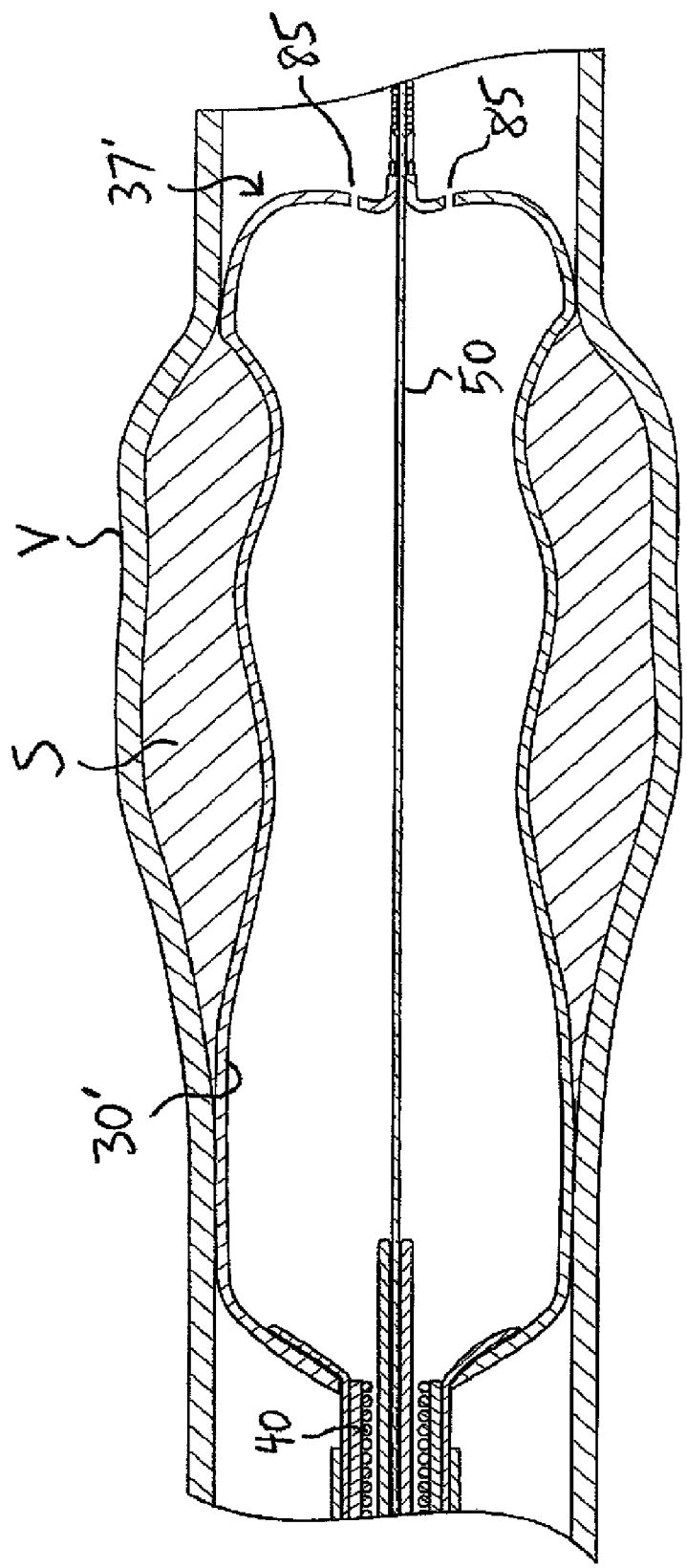
FIG. 14 is a side-sectional view of an alternative balloon that may be used to treat a vascular condition.

Referring now to FIG. 14, in an alternative embodiment of the present invention, balloon 30' comprises distal portion 37' having at least one perforation 85 pre-formed therein. Perforations 85 may be sized and configured to permit some inflation of balloon 30', yet when the balloon is inflated to a certain pressure, perforations 85 tear apart to separate distal portion 37' from attachment to core wire 50. Alternatively, perforations 85 may be configured to withstand full inflation of balloon 30', but after stent 40 expands within balloon 30', it applies a radially outward force that causes the perforations to give way. If perforations 85 are employed, it should be noted that distal cutting cannula 62 and shielding cannula 60 may be omitted. As will be apparent, perforations also may be disposed along a proximal portion of balloon 30' to cause separation upon application of a sufficient force, either by balloon inflation or expansion of stent 40.

It will be apparent that while the invention has been described primarily with respect to treatment of a stenosis within a vessel, the present invention may be used in other applications. For example, the apparatus and methods may be used in the treatment of aneurysms, e.g., by using balloon 30 to span the length of the aneurysm, seal it off, and employing internal stent 40 to provide structural support along the length of the aneurysm.

While various embodiments of the invention have been described, it will be apparent to those of ordinary skill in the art that many more embodiments and implementations are possible within the scope of the invention. Accordingly, the invention is not to be restricted except in light of the attached claims and their equivalents. Moreover, the advantages described herein are not necessarily the only advantages of the invention and it is not necessarily expected that every embodiment of the invention will achieve all of the advantaged described.

I claim:

1. Apparatus suitable for treating a vascular condition, the apparatus comprising:
   a balloon comprising proximal and distal regions, and further having uninflated and inflated states, wherein an inflation fluid is injectable to contact an inner surface of the balloon in the inflated state, and wherein the balloon is configured to expand and contact at least a portion of the vessel wall in the inflated state;
   a balloon shaft having proximal and distal ends;
   a core wire having proximal and distal ends, wherein the proximal region of the balloon is attached to the balloon shaft and the distal region of the balloon is attached to the core wire;
   a stent configured to be disposed within the balloon, the stent having contracted and expanded states, wherein the stent is configured to engage the inner surface of the balloon in the expanded state,
   wherein the stent is self-expanding, the apparatus further comprising a stent introducer disposed between the balloon shaft and the core wire, wherein the stent introducer is configured to radially restrain the stent prior to deployment from the contracted to the expanded state; and
   means for detaching at least a portion of the balloon after the stent expands from the contracted state to leave the portion of the balloon inside the vessel between the stent and an inner wall of the vessel.

2. The apparatus of claim 1 wherein the means for detaching comprises a distal cutting cannula having proximal and distal ends and a piercing element disposed at the distal end, the distal cutting cannula disposed annularly between the balloon shaft and the core wire.

3. The apparatus of claim 1 wherein the means for detaching comprises a proximal cutting cannula having proximal and distal ends and a piercing element disposed at the distal end, the proximal cutting cannula disposed for longitudinal movement over the balloon shaft.

4. The apparatus of claim 1 wherein the means for detaching comprises at least one perforation disposed in the distal region of the balloon.

5. The apparatus of claim 1 wherein at least a portion of the balloon comprises a collagenous extracellular matrix material to facilitate adhesion of the portion of the balloon with an intima of the vessel.

6. The apparatus of claim 5 wherein the collagenous extracellular matrix material comprises small intestinal submucosa.

7. A method suitable for treating a vascular condition, the method comprising:
   providing a balloon comprising proximal and distal regions;
   providing a balloon shaft having proximal and distal ends;
   providing a core wire having proximal and distal ends, wherein the core wire is disposed substantially within the balloon shaft, the distal end of the core wire extending past the distal end of the balloon shaft,
   wherein the proximal region of the balloon is attached to the balloon shaft and the distal region of the balloon is attached to the core wire;
   inflating the balloon, by injecting an inflation fluid that contacts an inner surface of the balloon, to at least partially dilate a vessel wall;
   providing a stent introducer disposed between the balloon shaft and the core wire;
   radially constraining a stent between the stent introducer and the core wire in a delivery configuration;
   positioning the stent introducer and the stent within at least a portion of the balloon;
   proximally retracting the stent introducer with respect to the balloon to cause the stent to radially expand against the inner surface of the balloon; and
   detaching at least a first portion of the balloon from a second portion of the balloon to leave the first portion of the balloon between the stent and the vessel wall.

8. The method of claim 7 further comprising:
   providing a distal cutting cannula having proximal and distal ends and a piercing element disposed at the distal end;
   disposing the distal cutting cannula annularly between the balloon shaft and the core wire; and
   distally advancing the distal cutting cannula to cause the piercing element to pierce through a distal portion of the balloon.

9. The method of claim 7 further comprising:
   providing a proximal cutting cannula having proximal and distal ends and a piercing element disposed at the distal end;
   disposing the proximal cutting cannula over the balloon shaft; and
   distally advancing the proximal cutting cannula with respect to the balloon shaft to cause the piercing element to pierce through a proximal portion of the balloon.

10. The method of claim 7 wherein detaching at least a first portion of the balloon from a second portion of the balloon comprises applying an internal pressure to tear apart at least one pre-formed perforation disposed in a distal region of the balloon.

11. The method of claim 7 further comprising providing a collagenous extracellular matrix on at least a portion of the balloon to facilitate adhesion of the portion of the balloon with an intima of the vessel.

12. Apparatus suitable for treating a vascular condition, the apparatus comprising:
    a balloon shaft having proximal and distal ends;
    a core wire comprising proximal and distal ends, wherein the core wire is disposed substantially within the balloon shaft, the distal end of the core wire extending past the distal end of the balloon shaft;
    a balloon having proximal and distal regions, and further having inflated and uninflated states, wherein an inflation fluid is injectable to contact an inner surface of the balloon in the inflated state, and wherein the proximal region of the balloon is attached to the balloon shaft and the distal region of the balloon is attached to the core wire;
    a stent configured to be disposed within the balloon, the stent having contracted and expanded states, wherein the stent is configured to engage an inner surface of the balloon in the expanded state; and
    means for detaching at least a portion of the balloon to leave the portion of the balloon inside the vessel, wherein the means for detaching comprises a distal cutting cannula having proximal and distal ends and a piercing element disposed at the distal end, the distal cutting cannula disposed annularly between the balloon shaft and the core wire, and wherein at least a portion of the balloon comprises a collagenous extracellular matrix material to facilitate adhesion of the portion of the balloon with an intima of the vessel.

13. The apparatus of claim 12 further comprising a proximal cutting cannula having proximal and distal ends and a piercing element disposed at the distal end, the proximal cutting cannula disposed for longitudinal movement over the balloon shaft.

14. Apparatus suitable for treating a vascular condition, the apparatus comprising:

a balloon comprising proximal and distal regions, and further having uninflated and inflated states, wherein an inflation fluid is injectable to contact an inner surface of the balloon in the inflated state, and wherein the balloon is configured to expand and contact at least a portion of the vessel wall in the inflated state;

a balloon shaft having proximal and distal ends;

a core wire having proximal and distal ends, wherein the proximal region of the balloon is attached to the balloon shaft and the distal region of the balloon is attached to the core wire;

a stent configured to be disposed within the balloon, the stent having contracted and expanded states, wherein the stent is configured to engage an inner surface of the balloon in the expanded state; and means for detaching at least a portion of the balloon after the stent expands from the uninflated state to leave the portion of the balloon inside the vessel between the stent and an inner wall of the vessel, wherein the means for detaching comprises a distal cutting cannula having proximal and distal ends and a piercing element disposed at the distal end, the distal cutting cannula disposed annularly between the balloon shaft and the core wire.

* * * * *